United States Patent
Surve

(10) Patent No.: US 8,099,797 B2
(45) Date of Patent: *Jan. 24, 2012

(54) DEPOSITION OF ELECTRONIC CIRCUITS ON FIBERS AND OTHER MATERIALS

(75) Inventor: Swatee N. Surve, Portland, OR (US)

(73) Assignee: NIKE, Inc., Beaverton, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 12/946,673

(22) Filed: Nov. 15, 2010

(65) Prior Publication Data

US 2011/0061150 A1    Mar. 17, 2011

Related U.S. Application Data

(63) Continuation of application No. 12/258,218, filed on Oct. 24, 2008, now Pat. No. 7,845,023, which is a continuation of application No. 10/077,548, filed on Feb. 14, 2002, now Pat. No. 7,845,022.

(51) Int. Cl.
*A41D 27/02* (2006.01)
*A41D 27/00* (2006.01)
*H05B 11/00* (2006.01)

(52) U.S. Cl. .............. 2/272; 2/243.1; 2/905; 607/115; 219/211

(58) Field of Classification Search .............. None
See application file for complete search history.

(56) References Cited

U.S. PATENT DOCUMENTS

| | | | |
|---|---|---|---|
| 3,586,597 A | | 6/1971 | Okuhashi |
| 3,632,966 A | | 1/1972 | Arron |
| 4,723,589 A | * | 2/1988 | Iyer et al. ............... 164/46 |
| 5,555,490 A | * | 9/1996 | Carroll .............. 361/679.03 |
| 5,636,378 A | | 6/1997 | Griffith |
| 5,655,223 A | | 8/1997 | Cozza |
| 5,771,492 A | * | 6/1998 | Cozza ..................... 2/161.2 |
| 5,906,004 A | * | 5/1999 | Lebby et al. ................. 2/1 |
| 6,006,357 A | * | 12/1999 | Mead ..................... 2/160 |
| 6,080,690 A | * | 6/2000 | Lebby et al. ............. 442/209 |
| 6,210,771 B1 | * | 4/2001 | Post et al. ............... 428/100 |
| 6,251,488 B1 | * | 6/2001 | Miller et al. ............ 427/596 |
| 6,472,029 B1 | * | 10/2002 | Skszek .................. 427/554 |
| 6,580,959 B1 | * | 6/2003 | Mazumder ............. 700/121 |
| 6,620,645 B2 | * | 9/2003 | Chandra et al. ............ 438/98 |
| 6,631,290 B1 | * | 10/2003 | Guck et al. .............. 600/509 |
| 6,853,293 B2 | * | 2/2005 | Swartz et al. ............ 340/5.92 |

* cited by examiner

*Primary Examiner* — Bobby H Muromoto, Jr.
(74) *Attorney, Agent, or Firm* — Banner & Witcoff, Ltd.

(57) ABSTRACT

Composite foams or leather materials (synthetic or natural) have electrical components deposited thereon. More particularly, one or more electrical components are formed directly onto the surface of the composite foam or the leather material. A group of transistors and piezoelectric components forming an accelerometer may be formed onto a surface of a composite foam or a leather material and incorporated into an article of wear.

42 Claims, 4 Drawing Sheets

DEPOSITION OF ELECTRONIC CIRCUITS ON FIBERS AND OTHER MATERIALS

RELATED APPLICATION DATA

This application is a continuation of U.S. patent application Ser. No. 12/258,218 filed Oct. 24, 2008 in the name of Swatee N. Surve and entitled "Deposition of Electronic Circuits on Fibers and Other Materials," which application is a continuation of U.S. patent application Ser. No. 10/077,548 filed Feb. 14, 2002 in the name of Swatee N. Surve and entitled "Deposition of Electronic Circuits on Fibers and Other Materials." These priority applications are entirely incorporated herein by reference.

FIELD OF THE INVENTION

The invention relates to the formation of electrical circuits on the surface of a fiber or other substrate material used to form an article of wear, such as clothing or shoes.

BACKGROUND OF THE INVENTION

Electrical devices are becoming ubiquitous in our society. People of all ages, from school children to senior citizens, regularly employ a variety of portable electronic devices. These devices include, for example, personal digital assistants, wireless telephones, and MP3 players. These portable devices also include time and athletic performance measurement devices, such as watches that monitor a wearer's heart rate, distance traveled, and speed. The use of these portable electronic devices has become so common that some clothing manufacturers have begun making articles of clothing (e.g., pants, suit jackets, etc.) with extra or specialized pockets for holding these portable electronic devices.

Even with additional or specialized pockets, however, transporting even a single portable electronic device may be inconvenient for a user. A runner or biker may prefer to use streamlined, form fitting clothing in order to improve his or her athletic performance, which may not provide an adequate location for storing or attaching a portable electronic device. In addition, the weight of the portable device itself, although relatively light, may still be bulky or uncomfortable for the user.

Accordingly, a variety of techniques have been proposed to integrate portable electrical devices into clothing. For example, U.S. Pat. Nos. 5,906,004 and 6,080,690 to Lebby et al., disclose textile fabric that includes a plurality of electrically conductive fibers, which may be used to induce either a wired or wireless coupling between the fabric and a portable electronic device. The fabric may also include one or more electronic sensors, or a plurality of sensing fibers. Similarly, U.S. Pat. No. 6,210,771 to Post et al., discloses fabrics formed of conductive fibers running along one weave direction and non-conductive fibers running along the opposite direction to give the resulting fabric selective, anisotropic electrical conductivity. The Post et al. patent further discloses using textile threads having selected electrical properties to form passive electrical components.

While these techniques offer a variety of advantages over the conventional packaging of portable electronic components into a single, centralized hand-sized container, they still have a number of limitations. For example, with each of the above-mentioned techniques, the fibers do not include complex electrical structures. Thus, additional circuitry, such as microprocessors or other control circuits, must be separately attached to the fabric and electrically connected to the conductive fibers employed by these techniques. Accordingly, there is a need to more fully integrate electronic circuits with a variety of wearable items, such as hats, clothing, and shoes, in order to provide portable electronic devices that are more comfortable for a user to transport or otherwise more convenient for use.

BRIEF SUMMARY OF THE INVENTION

Advantageously, various embodiments of the invention provide fibers, such as textile fibers, having electrical components deposited thereon. With these embodiments, one or more electrical components are formed directly onto the surface of at least one fiber. The fiber having the electrical component formed thereon may then be woven into a larger piece of fabric, which can be employed to produce an article of clothing. For example, a group of transistors and piezoelectric components forming an accelerometer may be woven onto one or more natural or synthetic fibers. The fibers may then be employed, for example as the warp, weft, or both, of a woven piece of fabric, or used to form a knitted piece of fabric. The fabric piece can then be cut and sewn to form a wearable item, such as a shirt, a pair of pants, a hat, or the upper piece of a shoe that includes the accelerometer.

DETAILED DESCRIPTION OF THE INVENTION

Figure 1:
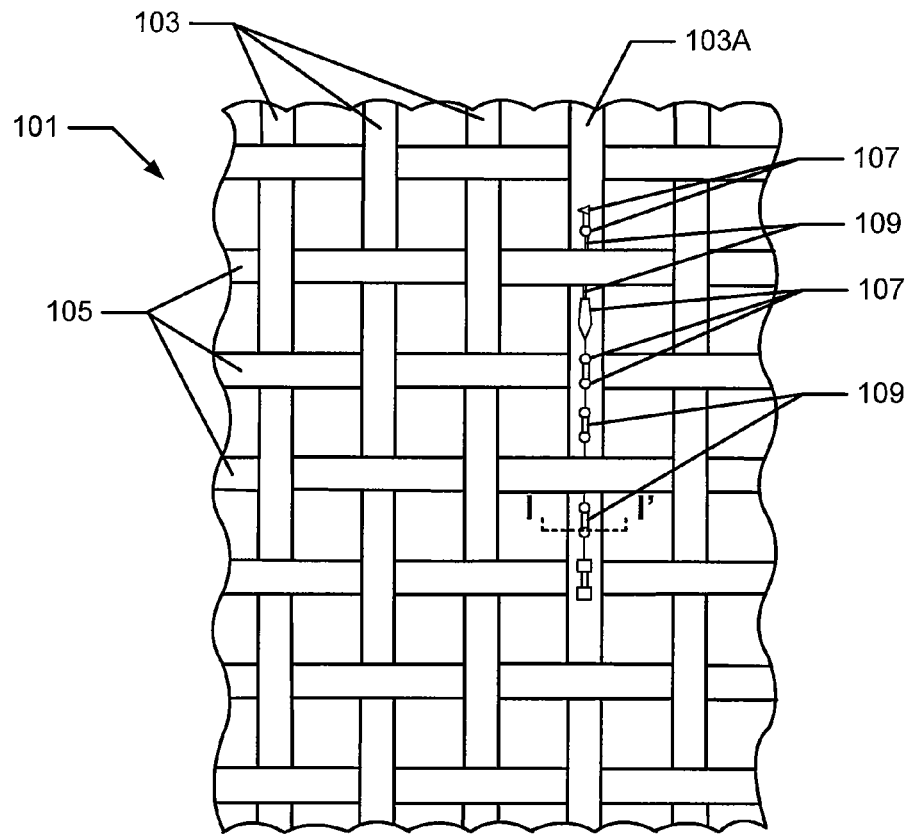
FIG. 1 illustrates a fabric woven from a fiber having electrical components formed thereon according to an embodiment of the invention.

FIG. 1 illustrates a textile material according to one embodiment of the invention. In this figure, a piece of woven fabric 101 includes warp fibers 103 and weft fibers 105. The fibers 103 and 105 may be any fibrous material suitable for forming wearable items. For example, one or more of fibers 103 and 105 may be natural fibers, such as cotton, wool, silk, or leather. One or more of fibers 103 and 105 may also be formed of any inorganic material suitable for weaving a fabric, such as, e.g., polyester, nylon, polypropylene, or rayon. Of course, the specific fiber materials listed above are for exemplary purposes only and should not be considered limiting.

As illustrated in FIG. 1, the warp fiber 103A has a number of electrical components 107 formed thereon. As will be explained in detail below, the electrical components 107 may be any type of structure that can be formed using conventional integrated circuit fabrication techniques. The electrical components 107 may be, for example, transistors, including bipolar junction transistors (BJTs) or field effect transistors (FETs), capacitors, resistors, inductors, antenna elements and piezoelectric crystals. Connection lines 109, which also are formed over the surface of the warp fiber 103A, then electrically interconnect the electrical components 107. Thus, the electrical components 107 may be interconnected by the connection lines 109 to form a desired electrical device, such as an accelerometer for measuring the acceleration of the fiber 103A in three dimensions.

It should be noted that, while the embodiment described herein relates specifically to a woven fabric, those of ordinary skill in the art will appreciate that a fiber having electrical components formed thereon, such as fiber 103A, may also be employed in fabrics formed from other types of interlaced fibers. For example, a fiber having electrical components formed thereon could be used to form a knitted fabric in accordance with the invention.

Figure 2:
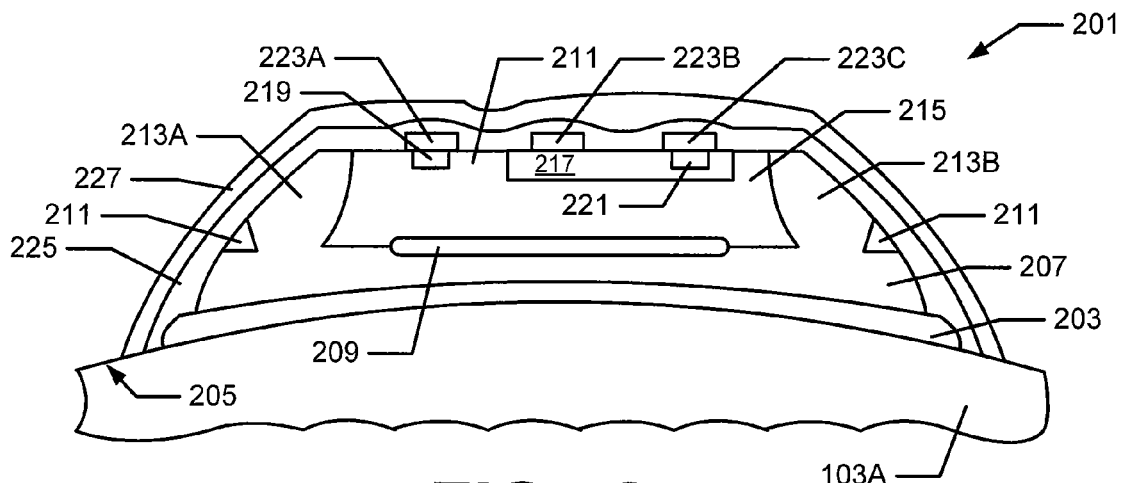
FIG. 2 shows a transistor formed on a fiber according to an embodiment of the invention.

FIG. 2 illustrates an enlargement and cross section of a portion the warp fiber 103A having an electrical component 107 (along line I-I' in FIG. 1). In particular, this figure illustrates a cross-section of one portion of the warp fiber 103A that has a NPN bipolar junction transistor 201 formed thereon. The structure of this transistor 201 will be discussed in detail below with reference to FIG. 2. Further, a method of forming the transistor 201 according to the invention will be discussed with reference to FIGS. 3A and 3B.

Figure 3A:
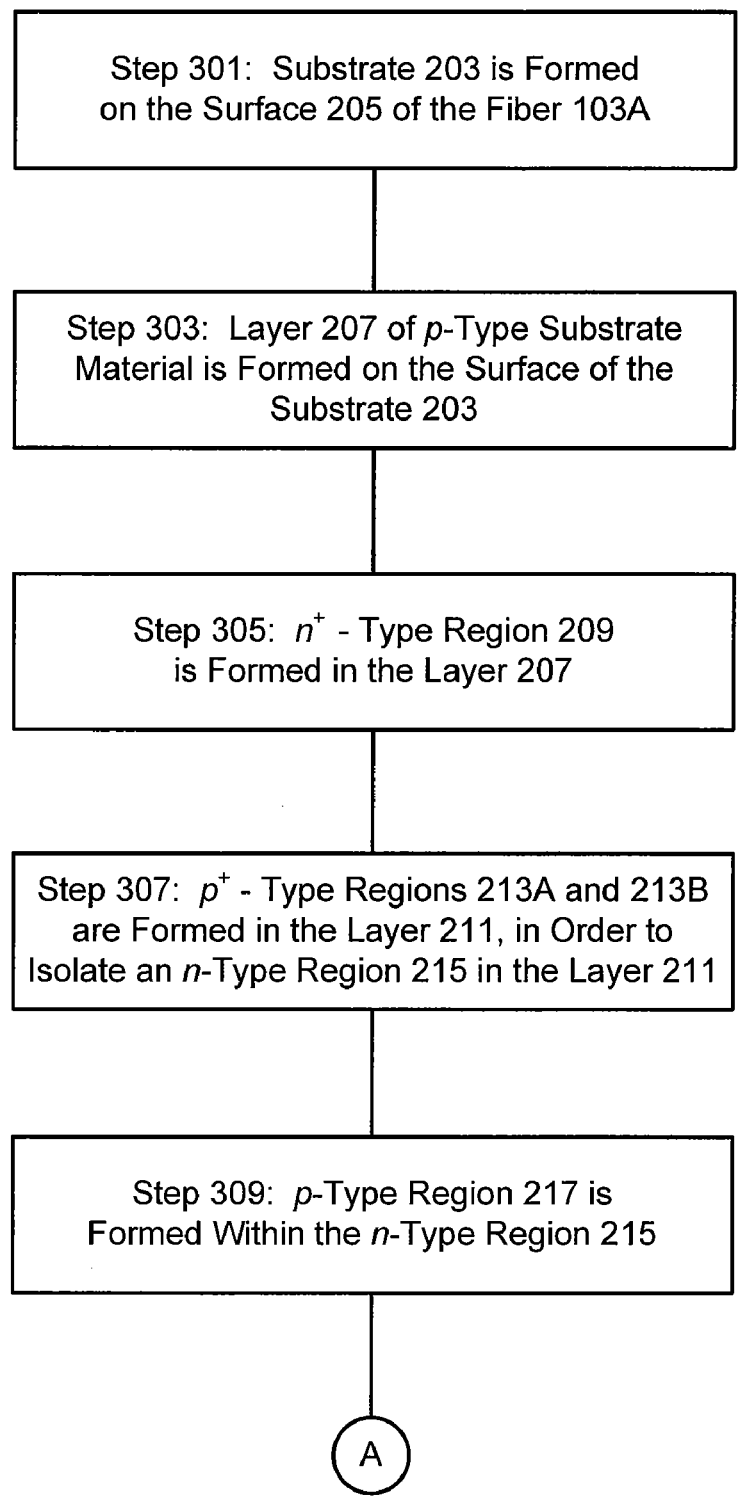
FIGS. 3A and 3B illustrate a method of forming an electrical component on a material for a wearable item according to an embodiment of the invention.
Figure 3B:
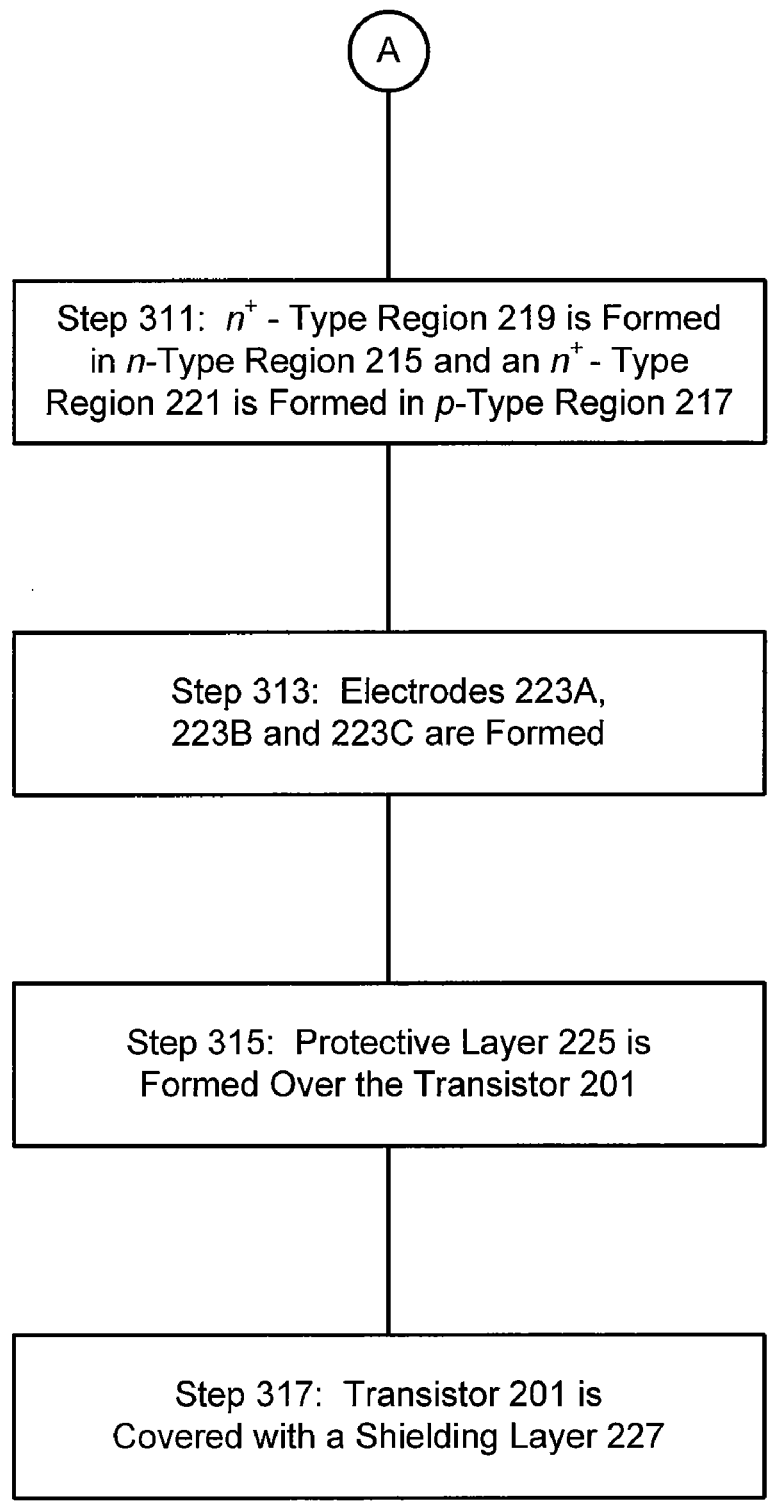

Referring now to FIG. 3A, in step 301, a substrate 203 is formed on the surface 205 of the fiber 103A. As seen in FIG. 2, the substrate 203 forms a base on the fiber 103A to support the transistor 201. The substrate 203 may be formed of any suitable material, including those materials typically used as a substrate in the conventional manufacture of conventional integrated circuits, such as metals, plastics, glasses, composite materials, and ceramics. In the particular embodiment illustrated in FIG. 2, the substrate 203 covers only a portion of the circumference of the fiber 103A. It should be noted, however, that with alternate embodiments of the invention, the substrate 203 may encompass the entirety of the circumference of the fiber 103A. While providing a substrate 203 that only partially covers the circumference the fiber 103A better allows the fiber 103A to retain its native properties (e.g., flexibility, appearance), covering the entire circumference of the fiber 103A may be useful in order to better adhere the substrate 203 to the surface 205 of the fiber 103A.

The use of the substrate 203 may provide a number of desirable advantages. First, the substrate 203 may be formed of a material that will provide a strong adherence of the transistor 201 to the fiber 103A. Moreover, the substrate 203 may be formed to provide a smooth surface upon which the transistor 201 can be deposited. This use of the substrate 203 to provide a smooth surface may be particularly beneficial where, e.g., the fiber 103A has an uneven or rough surface, such as commonly found with natural fibers. It should be noted, however, that for alternate embodiments of the invention, the substrate 203 may be omitted entirely. For example, where the material employed to form the bottom structure of the transistor 201 will strongly adhere to the surface of the fiber 103A, and the surface of the fiber 103A is sufficiently smooth to form the transistor 201 thereon, then the substrate 203 may be omitted.

Next, in step 303, a layer 207 of p-type substrate material is formed on the surface of the substrate 203. The layer 207 may be formed of any suitable material employed for conventional transistor fabrication, such as silicon. Further, the layer 207 of p-type substrate material may be doped as necessary for the transistor 201 to have the desired operating parameters.

The layer 207 may be formed according to a variety of methods. For example, the layer 207 may be formed using the techniques disclosed in U.S. Pat. No. 6,251,488 B1 to W. Doyle Miller et al., entitled "Precision Spray Process For Direct Write Electronic Components" and issued on Jun. 26, 2001, which patent is incorporated entirely herein by reference. In particular, this patent discloses techniques for depositing lines or layers of material by spraying the melted or semimolten material onto the desired surface. As described in detail in the Miller et al. patent, feedstock of the material to be deposited is sprayed at the deposition surface through a laser beam. The energy from the laser beam heats the feedstock, turning the material to a liquid or semimolten state. When the melted or semimolten material then strikes the deposition surface, it is deposited on that surface.

According to the invention, the techniques disclosed in the Miller et al. patent are applied to form electrical components on a fiber, such as the fiber 103A. As disclosed in the Miller et al. patent, the Miller et al. techniques can be used to deposit lines of material with a resolution as small as 0.1 microns. Typical cotton fibers are much larger, however, and have diameters ranging from 12.7 microns to 228 microns. Similarly, fine wool fibers have diameters of about 22 microns. Thus, according to the invention, the techniques taught in the Miller et al. patent can be used to form a variety of structures on fibers that can subsequently be woven into fabrics for articles of wear, such as hats, shoes, shirts, pants, etc.

As will be appreciated by those of ordinary skill in the art, the Miller et al. techniques can be used to form the layer 207 of material that has already been doped to possess the desired p-type characteristics. Alternately, the Miller et al. techniques can be used to form the layer 207 of undoped material. The layer 207 can then subsequently be doped to have the desired p-type characteristics using a suitable conventional doping technique, such as ion implantation or diffusion.

In step 305, an $n^+$-type region 209 is formed in the layer 207. Again, the $n^+$-type region can be formed using any suitable conventional doping technique, such as ion implantation or diffusion. Next, a layer 211 of n-type material is deposited over the layer 207 of p-type material. As with the formation of the layer 207 of p-type material, the Miller et al. techniques can be used to form the layer 211 of p-type material that has already been doped to possess the desired p-type characteristics. Alternately, the Miller et al. techniques can be used to form the layer 211 of undoped material, which can be doped to have the desired n-type characteristics using a suitable conventional doping technique, such as ion implantation or diffusion.

Next, in step 307, two $p^+$-type regions 213A and 213B are formed in the layer 211, in order to isolate an n-type region 215 in the layer 211. Then, in step 309, a p-type region 217 is formed within the n-type region 215, in order to create a base for the transistor 201. Subsequently, in step 311 (see FIG. 3B), an $n^+$-type region 219 is formed in n-type region 215 and an $n^+$-type region 221 is formed in p-type region 217, to create a collector and emitter, respectively, for the transistor 201. As previously noted, each of the doped regions 213A, 213B, 215, 217, 219 and 221 can be created using any suitable conventional doping technique, such as ion implantation or diffusion. Of course, $n^+$-type regions 219 and 221 may alternately be formed in different steps.

In step 313, the electrodes 223A, 223B and 223C are formed to provide the collector electrode, the base electrode, and the emitter electrode, respectively. The electrodes 223A, 223B and 223C can conveniently be formed using the techniques described in the Miller et al. patent referenced above. As will be appreciated by those of ordinary skill in the art, the electrodes 223A, 223B and 223C can be formed as part of connection lines 109, or they can be formed as individual contacts and then subsequently connected to connection lines 109.

Next, in step 315, a protective layer 225 is formed over the transistor 201. Because the fiber 103A is woven into the fabric 101, the fiber 103A (with the transistor 201) may rub against other fibers 103 and 105, or against an item being covered by the fabric (e.g., skin). Accordingly, with some embodiments of the invention, the protective layer 225 is preferably formed of a material that will be useful to protect the transistor 201 from damage through abrasion. Moreover, the fabric 101 may be used in an environment that is harmful to electrical components. For example, the fabric 101 may be used in a raincoat or in running clothing, potentially exposing the electrical components 107 to water, salts, acids, and other harmful substances. Thus, the protective layer 225 may additionally serve to protect the transistor 201 against contact with such harmful substances.

With the embodiment of the invention illustrated in FIG. 2, the material forming the protective layer 225 is nonconductive, as the layer 225 touches all three contacts 223A, 223B and 223C, and a conductive material might cause the contacts to short together. Thus, with this embodiment, the layer 225 may be formed of a suitable protective and nonconductive material, such as a resistive plastic resin, glass, or composite material. Of course, with alternate embodiments of the invention, the contacts 223A, 223B and 223C may be individually covered to prevent a short circuit by the protective layer, thereby allowing the protective layer 225 to be formed from a conductive or semiconductive material, such as a metal or carbon graphite. With still further embodiments of the invention, the protective layer 225 may be omitted altogether where abrasion or exposure protection is not desired.

Lastly, in step 317, the transistor 201 is covered with a shielding layer 227. As is known in the art, the shielding layer 227 is made from a conductive material, such as a conductive metal, to shield the operation of the transistor 201 from electromagnetic radiation. Like the protective layer 225, the shielding layer 227 is optional. If the protective layer 225 is formed of non-conductive material to protect the electrodes 223A, 223B and 223C from short-circuiting, then the shielding layer 227 is formed over the protective layer 225 with respect to the transistor 201. With this arrangement, the shield layer 227 can be used to protect the transistor 201 from abrasion or exposure. On the other hand, if the protective layer 225 is not used to electrically isolate the electrodes 223A, 223B and 223C, then the shielding layer 227 can be under the protective layer 225 with respect to the transistor 201, and the protective layer 225 can be used to protect the transistor 201 from abrasion or exposure.

It should be noted that the substrate 203, the protective layer 225 and the shielding layer 227 can each be created using the techniques disclosed in the Miller et al. patent referenced above. Because these structures do not require a high degree of resolution, however, these structures can also be formed using less precise techniques, such as simply dipping the fiber 203 in a liquid form of the material to be used for the substrate 203, the protective layer 225, or the shielding layer 227. These structures can also be formed by, e.g., conventional gas deposition, spraying, or any other suitable technique.

Figure 4:
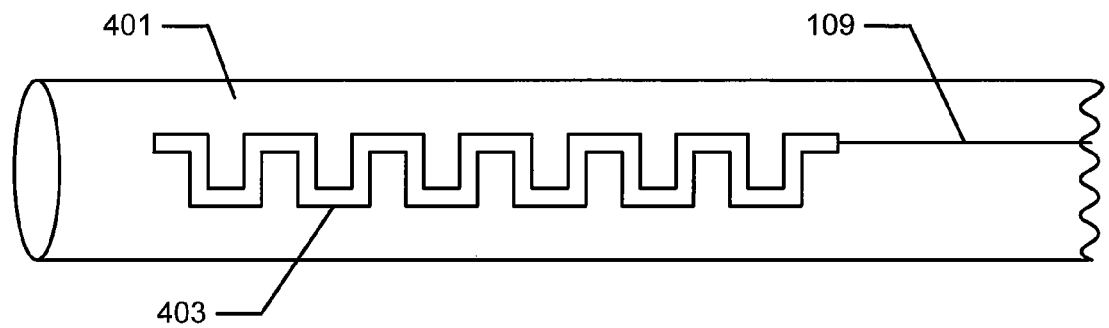
FIG. 4 illustrates a fiber having an antenna element formed thereon according to another embodiment of the invention.

While the above-described example relates to the formation of a bipolar junction transistor onto a fiber, those of ordinary skill in the art, upon reviewing this application, will appreciate that the teachings of the invention encompass forming a variety of electrical components onto a fiber. For example, as shown in FIG. 4, the technique disclosed in the Miller et al. patent can be used according to the invention to form a patterned line 403 on the fiber 401. Via a connection line 109, the patterned line 403 can be connected to other electrical components 107 that form an electrical device (not shown), so that the patterned line 403 acts as an antenna element for the electrical device. Still, further, the Miller et al. technique (or other suitable technique) can be used to form a layer of resistive material sandwiched between two layers of conductive material, to thereby form a capacitor. Thus, those of ordinary skill in the art will understand that, according to the teachings of the invention, any structure that can be fabricated using the Miller et al. technique or other suitable technique can be formed on a fiber in such a way that the fiber may be subsequently woven into a fabric for, e.g., clothing or other articles of wear.

Figure 5:
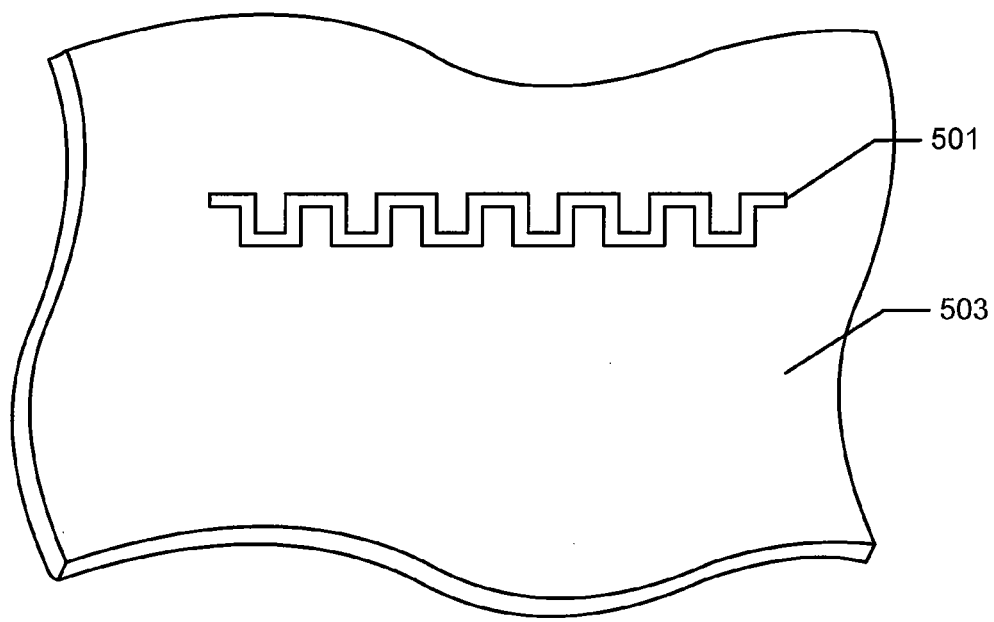
FIG. 5 illustrates an antenna element formed on a piece of leather according to still another embodiment of the invention.

According to still other embodiments of the invention, electrical circuits may be formed over the surface of other materials employed to make articles of wear, such as flexible materials commonly used in clothing. For example, as shown in FIG. 5, the Miller et al. technique can be used to form an antenna element 501 on a piece of leather 503. With this embodiment, the leather 503 then can be used as an article of wear, such as a jacket, a hat brim, or the upper portion of an athletic shoe. The antenna element 501 can be electrically connected to an electronic device (e.g., an accelerometer) associated with the article of wear to transmit and receive electrical signals.

Of course, those of ordinary skill in the art will appreciate that various embodiments of the invention may have electrical components formed on the surface of any material that can be employed in the construction of wearable items, including, but not limited to, natural and synthetic leathers, plastics, and composite foams. As with the embodiments of the invention described above, the electrical components formed on these non-fibrous materials may rest on a substrate layer, and may be covered with one or more protective layers, such as an insulating layer and/or a shield layer.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A method of forming an article of wear, comprising:
   forming a first electronic component and a second electronic component on a surface of a piece of composite foam;
   forming a first connection line on the surface of the piece of composite foam to connect the first electronic component and the second electronic component; and
   forming an article of wear including the piece of composite foam.

2. The method of forming an article of wear recited in claim 1, further comprising:
   forming a protective layer over the first and second electronic components.

3. The method of forming an article of wear recited in claim 1, further comprising:
   forming a substrate on the surface of the piece of composite foam, wherein the first and second electronic components are formed on a surface of the substrate.

4. The method of forming an article of wear recited in claim 1, wherein at least one of the first and second electronic components is a transistor.

5. The method of forming an article of wear recited in claim 1, further comprising:
   forming a third electronic component on the surface of the piece of composite foam; and
   forming a second connection line on the surface of the piece of composite foam to connect the second electronic component and the third electronic component.

6. The method of forming an article of wear recited in claim 5, further comprising:
  forming a substrate on the surface of the piece of composite foam, wherein the first, second, and third electronic components are formed on a surface of the substrate.

7. An article of wear, comprising:
  a piece of composite foam;
  a first electronic component on a surface of the piece of composite foam;
  a second electronic component on the surface of the piece of composite foam; and
  a connection line on the surface of the piece of composite foam connecting the first and second electronic components.

8. The article of wear recited in claim 7, further comprising:
  a protective layer over the first and second electronic components.

9. The article of wear recited in claim 7, wherein the surface of the piece of composite foam further includes a substrate thereon, wherein the first and second electronic components are provided on a surface of the substrate.

10. The article of wear recited in claim 7, wherein at least one of the first and second electronic components is a transistor.

11. The article of wear recited in claim 7, further comprising:
  a third electronic component on the surface of the piece of composite foam; and
  a second connection line connecting the second and third electronic components.

12. The article of wear recited in claim 11, wherein the surface of the piece of composite foam further includes a substrate thereon, wherein the first, second, and third electronic components are provided on a surface of the substrate.

13. A method of forming an article of wear, comprising:
  forming a transistor on a surface of a piece of composite foam; and
  forming an article of wear including the piece of composite foam.

14. The method of forming an article of wear recited in claim 13, wherein the transistor is formed on the surface of the piece of composite foam by spraying stock materials at the surface of the piece of composite foam through a laser.

15. The method of forming an article of wear recited in claim 13, further comprising:
  forming a substrate on the surface of the piece of composite foam, wherein the transistor is formed on a surface of the substrate.

16. The method of forming an article of wear recited in claim 13, wherein the transistor is a bipolar junction transistor.

17. The method of forming an article of wear recited in claim 13, wherein the transistor is an NPN bipolar junction transistor.

18. The method of forming an article of wear recited in claim 13, wherein the transistor is a field effect transistor.

19. The method of forming an article of wear recited in claim 13, further comprising:
  forming a first electronic component different from the transistor on the surface of the piece of composite foam; and
  forming a connection line on the surface of the piece of composite foam that interconnects the first electronic component with the transistor.

20. An article of wear, comprising:
  a piece of composite foam; and
  a transistor on a surface of the piece of composite foam.

21. The article of wear recited in claim 20, wherein the surface of the piece of composite foam further includes a substrate thereon, wherein the transistor is provided on the substrate.

22. The article of wear recited in claim 20, wherein the transistor is a bipolar junction transistor.

23. The article of wear recited in claim 20, wherein the transistor is an NPN bipolar junction transistor.

24. The article of wear recited in claim 20, wherein the transistor is a field effect transistor.

25. The article of wear recited in claim 20, wherein the surface of the piece of composite foam further includes an electronic component and a connection line, wherein the connection line connects the electronic component with the transistor.

26. A method of forming an article of wear, comprising:
  forming an antenna element on a surface of a piece of composite foam; and
  forming an article of wear including the piece of composite foam.

27. The method of forming an article of wear recited in claim 26, wherein the antenna element is formed on the surface of the composite foam by spraying stock materials at the piece of composite foam through a laser.

28. The method of forming an article of wear recited in claim 26, wherein the antenna element is formed as a patterned line on the surface of the composite foam.

29. The method of forming an article of wear recited in claim 26, further comprising:
  connecting a connection line to the antenna element.

30. The method of forming an article of wear recited in claim 26, further comprising:
  forming a substrate on the surface of the composite foam, wherein the antenna element is formed on the substrate.

31. An article of wear, comprising:
  a piece of composite foam; and
  an antenna element on a surface of the piece of composite foam.

32. The article of wear recited in claim 31, wherein the antenna element includes a patterned line.

33. The article of wear recited in claim 31, wherein the antenna element includes a connection line connected thereto.

34. The article of wear recited in claim 31, wherein the piece of composite foam further includes a substrate on its surface, wherein the antenna element is provided on the substrate.

35. A method of forming an article of wear, comprising:
  forming a capacitor on a surface of a piece of composite foam; and
  forming an article of wear with the piece of composite foam.

36. The method of forming an article of wear recited in claim 35, wherein the capacitor is formed by depositing a first conductive material layer on the surface of the piece of composite foam, depositing a first resistive material layer on the first conductive material layer, and depositing a second conductive material layer on the first resistive material layer.

37. The method of forming an article of wear recited in claim 35, wherein the capacitor is formed by depositing a first conductive material layer on the surface of the piece of composite foam by spraying the first conductive material through a laser, depositing a first resistive material layer on the first conductive material layer by spraying the first resistive material through a laser, and depositing a second conductive material layer on the first resistive material layer by spraying the second conductive material through a laser.

38. The method of forming an article of wear recited in claim 35, further comprising:

connecting a connection line to the capacitor.

39. The method of forming an article of wear recited in claim 35, further comprising:

forming a substrate on the surface of the piece of composite foam, wherein the capacitor is formed on the substrate.

40. An article of wear, comprising:

a piece of composite foam; and a capacitor on a surface of the piece of composite foam.

41. The article of wear recited in claim 40, wherein the capacitor includes a connection line connected thereto.

42. The article of wear recited in claim 40, wherein the surface of the piece of composite foam further includes a substrate on its surface, wherein the capacitor is provided on the substrate.

* * * * *